United States Patent [19]

Howard et al.

[11] 4,327,027
[45] Apr. 27, 1982

[54] CHEMICAL DETOXIFICATION OF TOXIC CHLORINATED AROMATIC COMPOUNDS

[75] Inventors: Kenneth J. Howard, North Little Rock; Albert E. Sidwell, Jacksonville, both of Ark.

[73] Assignee: Vertac Chemical Corporation, Memphis, Tenn.

[21] Appl. No.: 119,481

[22] Filed: Feb. 7, 1980

Related U.S. Application Data

[63] Continuation-in-part of Ser. No. 48,817, Jun. 15, 1979, abandoned.

[51] Int. Cl.$^3$ .................. C07D 317/44; C07C 37/68
[52] U.S. Cl. ............................ 260/340.3; 568/755
[58] Field of Search ............ 568/755; 260/701, 340.3; 203/6

[56] References Cited

U.S. PATENT DOCUMENTS

| | | | |
|---|---|---|---|
| 2,755,307 | 7/1956 | Nicolaisen | 568/755 |
| 2,843,601 | 7/1958 | Lorette | 260/340.6 |
| 3,011,940 | 12/1961 | Bollenback | 568/755 |
| 3,251,859 | 5/1964 | Knika | 260/340.3 |
| 3,399,215 | 8/1968 | Brader, Jr. | 260/340.6 |
| 3,909,365 | 9/1975 | Christena | 568/755 X |
| 4,142,943 | 3/1979 | Kohel et al. | 568/755 X |
| 4,228,309 | 10/1980 | Hatcher | 568/755 |

FOREIGN PATENT DOCUMENTS

| | | | |
|---|---|---|---|
| 2814126 | 10/1979 | Fed. Rep. of Germany | 568/755 |
| 401659 | 3/1974 | U.S.S.R. | 568/755 |

OTHER PUBLICATIONS

Chem. Abstracts 75:108800y D. G. Crosby et al.
Chem. Abstracts 76:12879a D. T. Williams et al.
Chem. Abstracts 79:18728j John Joseph Ford.

*Primary Examiner*—Ethel G. Love
*Attorney, Agent, or Firm*—Hammond & Littell, Weissenberger and Muserlian

[57] ABSTRACT

A method for the reduction of the content of toxic chlorinated aromatic compounds such as chlorinated aromatic dioxins and especially chlorinated dibenzo-p-dioxins in reaction products to virtually zero consisting essentially of reacting a mass containing chlorinated aromatic dioxins with an amount, in excess of stoichiometrical based on the total organic halogen content, of alkaline reactants selected from the group consisting of (1) alkali metal alcoholates of alcohols selected from the group consisting of alkanols having from 1 to 5 carbon atoms, polyalkoxyalkane glycols having 4 to 20 carbon atoms, alkanepolyols having from 2 to 5 carbon atoms and 2 to 3 hydroxyls, and monoalkyl ethers of such alkanepolyols with alkanols having from 1 to 4 carbon atoms, or (2) mixtures of said alcohols with alkaline reactants selected from the group consisting of alkali metal hydroxides and carbonates, at a reaction temperature of from 140° C. to 220° C. for a time sufficient to convert the organic halogen into inorganic halide, recovering a reaction mass essentially free of chlorinated aromatic dioxins, and optionally suspending said recovered reaction mass in water and extracting with an organic solvent to remove any minute residual chlorinated aromatic dioxins, and recycling said solvent extract to said reacting step.

14 Claims, 2 Drawing Figures

CHEMICAL DETOXIFICATION OF TOXIC CHLORINATED AROMATIC COMPOUNDS

This is a continuation-in-part of Ser. No. 48,817, filed June 15, 1979, and now abandoned.

BACKGROUND OF THE INVENTION

This invention relates to a process for dehalogenation of chlorinated aromatic dioxins and related compounds in a safe and economic manner. Since toxicity of chlorinated dibenzo-p-dioxin and many other compounds is reported to be related to the number of halogen atoms, dehalogenation to produce polyphenolic compounds reduces their toxicity. Specifically, 2,3,7,8-tetrachlorodibenzo-p-dioxin is claimed to be highly toxic and the detoxification and destruction method described herein is especially suitable for destruction of that compound.

In the production of 2,4,5-trichlorophenol (2,4,5-TCP), varying amounts of 2,3,7,8-tetrachlorodibenzo-p-dioxin (TCDD) are produced as a contaminant. The production of 2,4,5-TCP is generally by the dechlorination of symetrical tetrachlorobenzene. This is usually accomplished in the presence of methanolic caustic followed by acidulation of the corresponding phenolate according to the following generalized reactions

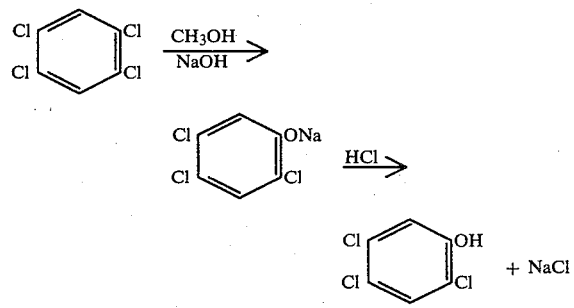

During the first reaction step varying amounts of dichlorodimethyoxybenzene also are produced, but, in addition, under the reaction conditions, two mols of sodium trichlorophenate may react to yield TCDD according to the reaction

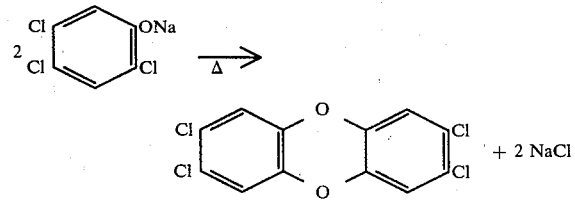

By careful distillation the 2,4,5-TCP can be recovered from the reaction mass containing dichlorodimethoxybenzenes and TCDD. The TCDD can also be separated from the 2,4,5-TCP by adsorption on an activated adsorbant such as activated carbon. However, TCDD is claimed to be extremely toxic and cannot readily be disposed of.

No other method of chemical destruction or degradation of TCDD is known which will, quantitatively, safely and economically destroy TCDD in the presence of a wide range of associated materials. TCDD is a highly stable compound. Its destruction by incineration is a possibility which is presently being investigated. However, incineration of a highly chlorinated compound is difficult and does present the possibility of contamination of either the scrubber liquor, the exhaust gases, or any solid residues.

Many methods of chemical destruction of TCDD were investigated, including rupture of the ether linkages, rupture of the aromatic ring structure, chemical oxidation, replacement of the halogen atoms, and ultraviolet light degradation. Throughout this work the complexity of the waste streams containing TCDD interfered with or negated many commonly accepted chemical reaction systems. For example, it is well known that TCDD in dilute proton donating solutions in thin clear films is rapidly decomposed by ultra-violet light. However, the dark viscous streams being investigated yielded little or no TCDD decrease with time. Rupturing the ether linkage with HBr and HI was accomplished only very slowly and incompletely with an extrapolated large expense for reagents.

Replacement of the chlorine atoms with the sodium salt of hydroxyl groups has proven to be fast (a few hours as opposed to days for other methods), safe (can be accomplished at atmospheric pressure with no gaseous emissions to be scrubbed or neutralized), economic (uses cheap raw materials which are readily available), and most of all, complete in a wide range of normally occurring contaminants.

In addition to TCDD, other chlorinated aromatic dioxins and many other chlorinated organic compounds are produced as toxic by-products in the production of industrial organic chemicals. It is obvious to those skilled to the art that these materials may also be disposed of utilizing the concept of this invention.

OBJECTS OF THE INVENTION

An object of the present invention is the development of methods for chemical destruction or degradation of toxic halogenated aromatic compounds.

Another object of the present invention is the development of a method for the reduction of the content of chlorinated dibenzo-p-dioxins in reaction products to virtually zero consisting essentially of reacting a mass containing chlorinated dibenzo-p-dioxins with an amount, in excess of stoichiometrical based on the total organic halogen content, of alkaline reactants selected from the group consisting of (1) alkali metal alcoholates of alcohols selected from the group consisting of alkanols having from 1 to 5 carbon atoms, alkoxyalkane glycols having 4 to 6 carbon atoms, alkanepolyols having from 2 to 5 carbon atoms and 2 to 3 hydroxyls, and monoalkyl ethers of such alkanepolyols with alkanols having from 1 to 4 carbon atoms, or (2) mixtures of said alcohols with alkaline reactants selected from the group consisting of alkali metal hydroxides and carbonates, at a reaction temperature of from 140° C. to 220° C. for a time sufficient to convert the organic halogen into inorganic halide, recovering a reaction mass essentially free of chlorinated dibenzo-p-dioxins, and optionally suspending said recovered reaction mass in water and extracting with an organic solvent for chlorinated dibenzo-p-dioxins immiscible in water and recycling said organic solvent extract to said reacting step.

These and other objects of the invention will become more apparent as the description thereof proceeds.

THE DRAWINGS

DESCRIPTION OF THE INVENTION

Figure 1:
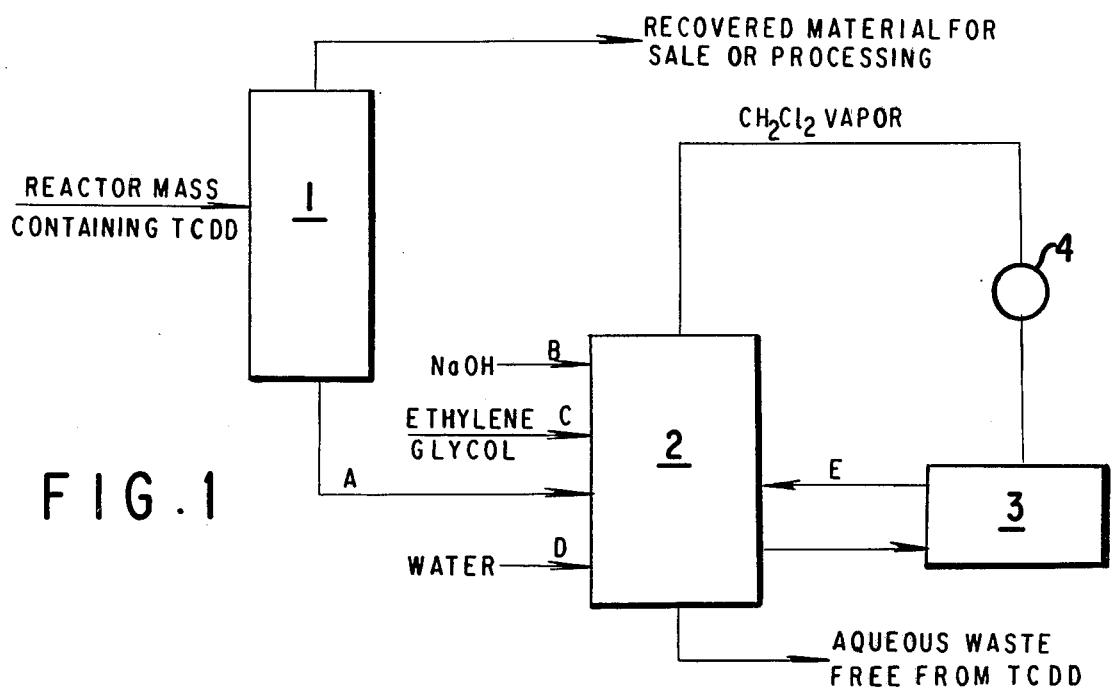
FIG. 1 is a flow diagram of one recycling chlorinated dibenzo-p-dioxin destruction apparatus.

The above objects have been achieved by the present invention involving dehalogenation of 2,3,7,8-tetrachlorodibenzo-p-dioxin, other chlorinated dibenzo-p-dioxins and other halogenated aromatic compounds preferably at atmospheric pressure, using anhydrous alkali metal salts of alcohols, preferably polyhydroxy alcohols. Dehalogenation may also be accomplished by reacting a mixture of halogenated aromatic compounds, an alcohol, and a water solution of an alkali metal hydroxide.

It is the purpose of this invention to detoxify waste materials containing chlorinated dibenzo-p-dioxins by destroying them. The practice of this invention causes a substantial reduction in chlorinated dibenzo-p-dioxin concentration in reaction streams toxified by them. Usually over 95% of the amount of chlorinated dibenzo-p-dioxin originally present is destroyed in one cycle and by recycling, up to essentially 100% of the chlorinated dibenzo-p-dioxin originally present is destroyed.

In some cases the amount of chlorinated aromatic dioxin remaining after one cycle treatment is virtually zero, being undetected by methods sensitive to one part per billion level or less. When using the method to destroy TCDD, because of high toxicity it is preferable to continue the reaction until no detectable TCDD is present. For other chlorinated aromatic dioxins, treatment may be stopped while some chlorinated aromatic dioxin is still detectable. In other cases where chlorinated aromatic dioxins less toxic then TCDD are to be removed, it may suffice to remove them to a level of perhaps 1 to 20 parts per billion or even higher concentrations. Therefore, the degree of removal desired and the desired final chlorinated aromatic dioxin concentration depends on the costs, circumstances, and toxicity surrounding their removal. In this disclosure the final desired concentration that is required to suitably detoxify the material to be treated is referred to as "virtually zero".

More particularly, the present invention involves a method for the reduction of the content of 2,3,7,8-tetrachlorodibenzo-p-dioxin and chlorinated dibenzo-p-dioxins, in reaction product waste stream and after isolation from desired products, to virtually zero consisting essentially of reacting a reaction mass containing more than 100 parts per billion of 2,3,7,8-tetrachlorodibenzo-p-dioxin with an amount, in excess of stoichiometrical, based on the halogen content, of alkaline reactants selected from the group consisting of (1) alkali metal alcoholates of alcohols selected from the group consisting of alkanols having from 1 to 5 carbon atoms, polyalkoxyalkane glycols having 4 to 20 carbon atoms, alkanepolyols having from 2 to 5 carbon atoms and 2 to 3 hydroxyls, and monoalkyl ethers of such alkanepolyols with alkanols having from 1 to 4 carbon atoms, or (2) mixtures of said alcohols with alkaline reactants selected from the group consisting of alkali metal hydroxides and carbonates, at a reaction temperature of from 140° C. to 220° C. for a time sufficient to convert the organic halogen into inorganic halide, recovering a reaction mass essentially free of 2,3,7,8-tetrachlorodibenzo-p-dioxin and other chlorinated dibenzo-p-dioxins, and optionally suspending recovered reaction mass in water and extracting with an organic solvent for chlorinated dibenzo-p-dioxin immiscible in water and recycling said organic solvent extract to said reacting step.

In the process of the invention, it is preferable to employ at least two equivalents of an alkali metal salt of the alcohol for every equivalent of organic halogen, preferably with an excess of the alcohol of one-half to one equivalent. The reaction mass, in a reactor, is brought to the reaction temperature and held until the organic halogen has been converted into inorganic halide. This usually requires up to 200 hours, preferably from 1 to 12 hours, depending upon the reaction temperature and the content of organic halogen.

The suitable temperature range for treating chlorinated dioxin containing liquids with alkali metal alcoholates is between about 140° C. and 220° C. However, there is no clear cut limit to either the upper or lower temperature. At higher temperature, some organic material begins to char and handling can be a problem. In such a case, shorter times are used as the temperature exceeds 220° C., but higher temperatures are within the practice of this invention. For temperatures below 140° C., the reaction rate is slow and days, weeks, or even months might be required to affect the desired change. Thus, normally, the invention will be practiced between 140° C. and 220° C., but it could also be practiced outside that range as described above. Preferably the alcohol is a polyhydric alcohol in order that the reaction can take place at atmospheric pressure. Of course, with lower molecular weight alcohols, autoclaves or high pressure flow reactors can be employed under superatmospheric pressures.

The process is preferably conducted with the alkali metal alcoholates of alkanespolyols having from 2 to 5 carbon atoms and 2 to 3 hydroxyls. By the use of the alcoholate, no by-product water is produced.

Preferably the alkali metal alcoholate employed is sodium ethylene glycolate, which is slowly added to the reaction mass over a period of time. Other alkali metal alcoholates may be employed such as potassium, or even the other alkali metals such as lithium, rubidium, cesium. The costs of the latter, however, usually rule against their use.

The alkali metal alcoholate may be produced in a conventional manner by reacting an aqueous solution of an alkali metal hydroxide such as sodium or potassium hydroxide with an alkanepolyol such as ethylene glycol or an alcohol in the presence of an azeotropic solvent under azeotropic distillation conditions, removing the water present and formed. It may also be formed by reacting alkali metal with the polyol or alcohol.

When the alkali metal alcoholate is utilized in the reaction of the invention, it is employed in the presence of one-half to one equivalent of the free alcohol per equivalent of organic halogen.

The polyhydroxyalcohols which have been demonstrated to dehalogenate organic halogens, such as to dechlorinate TCDD, include alkanepolyols having 2 to 5 carbon atoms and 2 to 3 hydroxyl groups, such as ethylene glycol, propylene glycol, glycerine, and various mixtures; polyalkoxyalkane glycols having from 4 to 20 carbon atoms, such as diethylene glycol. Crude glycol mixtures, monoalcoholic ethers of glycol and glycerine also yield a satisfactory reaction at atmospheric pressure. Methyl, ethyl, and propyl alcohols can also be utilized, but their use requires pressures greater than atmospheric.

The reaction is exothermic and should be controlled by either slow addition of one of the reagents or slow removal of by-product water rather than depending upon cooling. The reaction temperature ranges from 140° C. to 220° C., depending upon the boiling point of the various materials in the reaction mass and time available for complete dehalogenation.

The ratio of alkali metal salt of the alcohol to the organic halogens may range from 1.0 upward to over 2.0. Use of a 2.0 ratio results in a reaction mass which reduces the difficult job of analyzing for trace TCDD residuals. Excess polyhydroxylalcohol may range from 0 to over 1 equivalent per equivalent organic halogen. Its use is desirable for reaction mass fluidity and would not be necessary for more fluid organic halogens.

The dechlorination of TCDD is believed to be a two-step reaction which may be represented by the following equations, assuming that sodium ethylene glycolate is employed:

1. TCDD + 4 NaOC$_2$H$_4$OH $\longrightarrow$ (I)

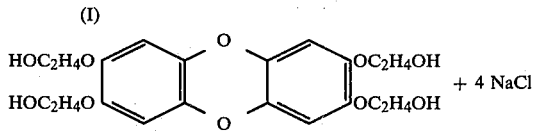
+ 4 NaCl (II)

2. (II) + 4 NaOC$_2$H$_4$OH $\longrightarrow$

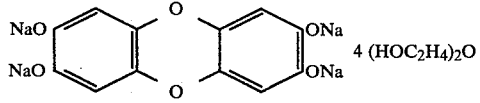
4 (HOC$_2$H$_4$)$_2$O (III)

Reaction step (1) demonstrates that TCDD has been chemically destroyed with only one equivalent of sodium ethylene glycollate per chlorine. Chloride analysis would show complete conversion from organic to inorganic chloride. However, the resulting product (II) would be difficult to separate from any residual traces of TCDD for a standard gas-liquid chromatograph analysis. If the present methods of analysis can be modified so as to determine TCDD in the presence of compounds such as (II), a significant reduction in reagent quantities could be realized. Also the dehalogenation of other materials may not require complete conversion to compounds such as compound (III) and therefore would require less reagents for destruction.

Continued reaction as in Step (2) results in compounds such as represented by (III) which are highly water-soluble in the alkaline state. Any residual TCDD can be easily extracted from the alkaline water solution and the concentration determined by standard analyses. By-product diethylene glycol is also water-soluble.

If a minute residual amount of TCDD is present, it can be extracted from the alkaline water solution by a water immiscible organic solvent for chlorinated dibenzo-p-dioxins and recycled to a further reaction with reaction step (I). This is particularly important where large volumes of reaction masses containing chlorinated dibenzo-p-dioxins or TCDD are being produced on a regular production basis.

As a variant on the basic process and as indicated above, the process can be operated on a continuous or batch basis employing a reaction zone for reaction step (I) to which is fed the reaction mass containing chlorinated dibenzo-p-dioxins as well as the organic solvent extract of the alkaline water solution, the organic solvent is recovered by distillation and the reaction mass containing a fortified amount of chlorinated dibenzo-p-dioxins is treated by the alcoholate treatment with formation of product (III) which is dissolved in an alkaline solution and extracted with the recycling organic solvent. By this method essentially no chlorinated dibenzo-p-dioxins remain in the aqueous alkaline solution which may then be discharged.

This process may be utilized, by anyone skilled in the art, for safe disposal of TCDD, and other toxic halogenated compounds. It produces water-soluble salts of polyhydroxyaromatic compounds which may be more swiftly decomposed by aerobic bacteriological action than the original toxic insoluble stable compounds. The sodium phenolate type derivative formed from the chlorinated dioxins may be acidified to form organic phenol type compounds and inorganic salts. The organic materials so formed can be separated and safely incinerated. The long-term stability of many toxic aromatic halogen materials such as TCDD, PCB, and PBB has prevented disposal by landfill methods. Incineration of TCDD requires extraordinary controls and checks to assure that total destruction has been achieved and no contamination of voluminous off-gases, scrubber effluent or ashes occurred.

Dehalogenation by this method can be safely accomplished using laboratory glassware to dispose of small research quantities of toxic halogenated compounds. Alternate disposal methods, if any other methods are available to the researcher, require meticulous handling, and expensive shipping procedures.

Removal of TCDD from commercial materials and wastes has been demonstrated by several means, including activated carbon adsorption and others. But ultimate disposal of these concentrated wastes has been stymied for lack of demonstrated safety.

The present process can be employed to detoxify the distillation bottoms resulting from the distillation of 2,4,5-TCP. It is known that incineration or other heat treatment of 2,4,5-TCP causes formation of TCDD.

It is known that chlorinated dibenzo-p-dioxins in solutions or melts of other materials can be adsorbed on carbon to remove them from the solution. Thus, chlorinated dibenzo-p-dioxins present as only a few parts per million in Agent Orange can be concentrated to a concentration of several percent adsorbed on carbon. The disposal of carbon containing highly chlorinated dibenzo-p-dioxin content presents a problem because burial of such material is undesirable, and incineration is impractical and has not been safely practiced yet to remove traces of chlorinated dibenzo-p-dioxin.

We have found that adsorbed chlorinated dibenzo-p-dioxins can be removed from carbon by extraction with hot organic solvents and the solvents treated by method described herein to destroy the clorinated dibenzo-p-dioxins. Suitable solvents are benzene, toluene, xylene, or higher molecular weight aromatic solvents, or their derivatives containing organic halogen, nitrogen, and oxygen. If the solvent containing the eluted chlorinated dibenzo-p-dioxin is a high boiling solvent (b.p. over 150° C.), it may be directly treated with the alkali metal alcoholate solution to destroy the chlorinated dibenzo-p-dioxin. If the solvent has a boiling point below about 150° C., the direct treatment with alcoholate may be done under autogenous pressure or a small amount of high boiling material such as dichlorodimethoxybenzene or heavy naptha may be added to the solvent-chlorinated dibenzo-p-dioxin solution and that solution distilled to form a residue that boils above 150° C. The portion boiling above about 140° C. may be treated with the alkali metal alcoholates to destroy the chlorinated dibenzo-p-dioxins.

Sorbents suitable for adsorbing chlorinated dioxins are microporous materials such as activated carbon, activated alumina, silica zerogels, silica-alumino xerogels, large pore zeolites, like zeolite Y, X and mordenite, and many other materials that are characterized by pore diameters in the range of 7 to 1000 Å and surface areas in the range of 25 to 1,500 m$^2$/gm. For best results the sorbent should be resistant to non-aqueous alkaline fluids at temperatures in the range of 140° to 220° C., and in this respect activated carbon is an especially suitable material.

The process operated as a continuous or batch process with recycling can be more particularly described with reference to FIGS. 1 and 2 which show two variants of a recycling solvent process.

In either process, the reaction mass containing chlorinated dibenzo-p-dioxins, such as TCDD is carefully distilled to remove the desired product such as 2,4,5-TCP in a distillation column 1. The product and any solvents present are distilled off, leaving a high boiling residue containing chlorinated dibenzo-p-dioxins such as TCDD as a still bottom. This residue A, together with sodium hydroxide B, ethylene glycol (C) is charged into the destructor autoclave 2 and reacted as discussed above. After the reaction is completed, water D is charged in.

Figure 2:
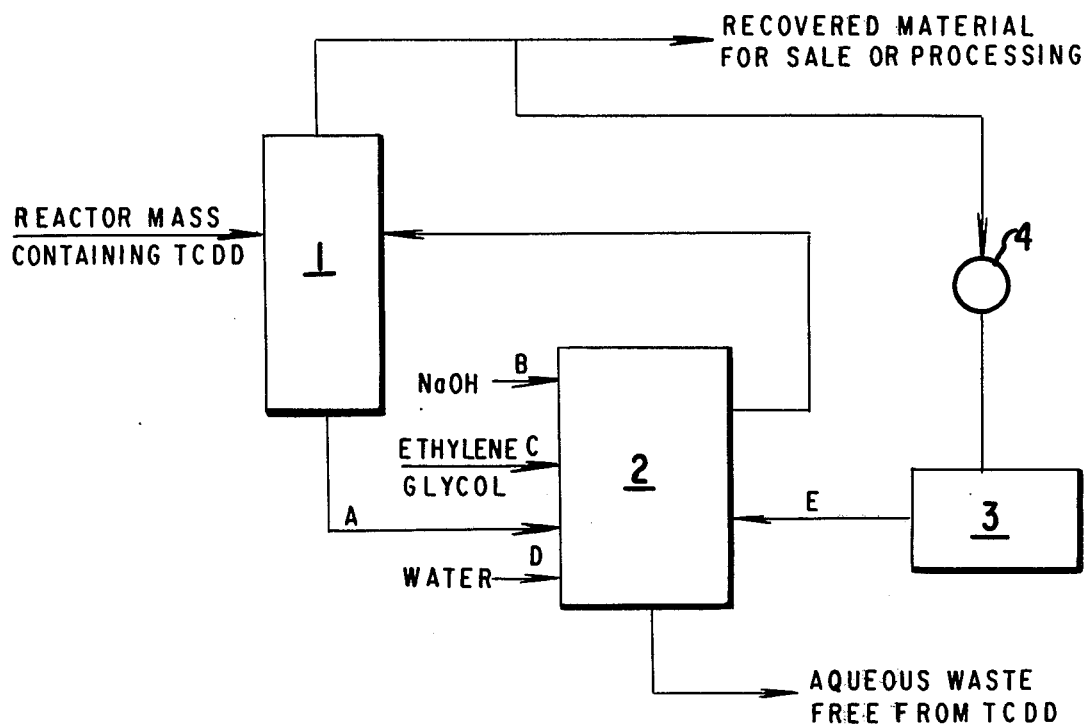
FIG. 2 is a flow diagram of another recycling chlorinated dibenzo-p-dioxin destruction apparatus.

In the embodiment of FIG. 1, the reaction is conducted to a point where the TCDD content is less than 100 ppb. The aqueous mass in the destructor autoclave 2 is extracted with a relatively low boiling organic solvent for chlorinated dibenzo-p-dioxins (E) such as methylene chloride which is stored in the container 3. After mixture with agitation for extraction of residual chlorinated dioxins the mixture is allowed to settle and the aqueous phase was found to contain less than 1 ppb of TCDD. This is then discarded. The methylene chloride containing extracted chlorinated dibenzo-p-dioxins was returned to the storage container 3. When a second batch of distilled reaction residue A was treated in the destructor autoclave 2, after charging the sodium hydroxide (B) and the ethylene glycol (C), the methylene chloride extract (D) from the preceding batch was charged. On heating the autoclave 2, the methylene chloride evaporates. The methylene chloride vapor is condensed in the condensor 4 and returned to the storage container 3 for use in extracting the aqueous mass from the reaction of the second batch in the destructor autoclave 2. The recycling procedure is continued from batch to batch with essentially 100% recovery of the recycling methylene chloride and discharge of an aqueous waste containing less than 1 ppb of TCDD.

In the embodiment of FIG. 2, again the reaction in the destructor autoclave 2 is continued to a point where the TCDD content is less than 100 ppb. The aqueous mass in the destructor autoclave is extracted with a medium boiling organic solvent for chlorinated dibenzo-p-dioxins (E) such as toluene or hexane which is stored in the storage container 3. After mixture with agitation for extraction of residual chlorinated dioxins, the mixture is allowed to settle and the aqueous phase was found to contain less than 1 ppb of TCDD. This is then discarded. The solvent containing extracted chlorinated dibenzo-p-dioxins was passed to the distillation column 1 where the solvent is distilled off with the desired 2,4,5-TCP, separated therefrom, condensed in condenser 4 and returned to the storage container 3. The recycling procedure is continued where the distillation column 1 is operating on a continuous basis.

The process of the invention is useful for the dehalogenation of a wide range of halogenated aromatic compounds. It has been employed to destroy TCDD, chloro-substituted phenolic esters, chlorinated benzenes, 2,4,5-T acid and other compounds associated with the manufacture of 2,4,5-trichlorophenol. Use of the process can be made in research and laboratory facilities and in commercial processes with proper preconcentration of the TCDD, or other undesirable toxic halogenated compounds.

A large number of toxic halogenated compounds are difficult to safely dispose of by existing methods. Such materials are often difficult to decompose by bacteriological action due to low solubilities in water and the presence of the halogen atoms. Disposal by landfill presents the hazard of their being re-introduced into the environment at some later time. Incineration of highly halogenated materials requires special designs to avoid high corrosivity and maintenance. Incineration must be carefully monitored to avoid environmental pollution by incomplete combustion.

The following examples are illustrative of the practice of the invention without being limitative in any manner.

EXAMPLE 1

207 gms of dichlorodimethoxybenzene still bottoms containing 100 milligrams of TCDD (34.25% chlorine as organic chlorine) were introduced into a three-necked, 1,000 ml, round-bottomed flask equipped with a thermometer, a reflux condenser with a water trap sidearm, magnetic stirrer, and a heating mantle.

Thereafter, 20 ml of toluene, 160 gms of anhydrous NaOH, and 372 gms of ethylene glycol were introduced. The mixture was heated to 175° C. while withdrawing 72 gms of water from the water trap. The temperature was maintained at 175° C. for a total of six hours.

Analysis of the resulting mass showed a total conversion of organic to inorganic chloride, with no TCDD detectable by analysis with instruments that will detect 1 part per billion.

EXAMPLE 2

248 gms of ethylene glycol, 20 ml of toluene, and 320 gms of a 50% aqueous NaOH were introduced into a 1,000 ml flask equipped as in Example 1. The temperature of the reaction mass was raised until refluxing commenced. The temperature was slowly increased to 175° C. while removing 232 gms of water. After cooling, 336 gms of sodium ethylene glycolate were obtained. This product was flaked before further use.

207 gms of dichlorodimethoxybenzene still bottoms containing 100 milligrams of TCDD (34.25% chlorine as organic chlorine) were introduced into a 1,000 ml flask equipped as in Example 1. 62 gms of ethylene glycol were added and the temperature of the reaction was raised to 175° C. The 336 gms of the flaked sodium ethylene glycolate were slowly added over a two-hour period to the reaction mass maintained at a temperature of 175° C. The reaction temperature was maintained for an additional four hours.

Analysis of the resultant mass showed a total conversion of organic to inorganic chloride, with no TCDD detectable.

EXAMPLE 3

207 gms of dichlorodimethoxybenzene still bottoms containing 100 milligrams of TCDD (34.25% chlorine as organic chlorine) were introduced into a 1,000 ml flask equipped as in Example 1. 20 ml of toluene, 320 gms of a 50% aqueous solution of NaOH, 248 gms of ethylene glycol, 76 gms of propylene glycol, and 106 gms of diethylene glycol were added thereto. The mixture was slowly heated to 175° C. while azeotropically distilling and withdrawing 232 gms of water from the water trap. The temperature was maintained at 175° C. for a total of six hours.

Analysis of the resulting mass showed a total conversion of organic to inorganic chloride, with no TCDD detectable.

EXAMPLE 4

200 gms of residue rich in chlorinated anisoles containing 43.1% organic chlorine and 39.7 ppm of TCDD were introduced into a 2,000 ml autoclave equipped with an agitator, heating mantle, thermocouple and pressure gauge together with 400 gms of sodium methylate and 350 gms of methanol.

The mixture was heated to 160° C. During the heating period the pressure rose to 245 psig. The contents were held at 160° C. for 4½ hours. The autoclave was cooled, emptied, and the contents analyzed.

Analysis of the resulting mass showed a total conversion of TCDD of 96.3%.

EXAMPLE 5

2,000 gms of a mixture of 50% butyl 2,4-dichlorophenoxyacetate and 50% butyl 2,4,5-trichlorophenoxyacetate, known as Agent Orange, and containing 7 ppm of TCDD was passed at ambient temperature through 80 gms of 14 to 28 mesh activated carbon having a surface area of about 400 m$^2$/gm. The carbon was in the form of a supported fixed bed in a glass column 32 mm diameter. Complete removal of TCDD from Agent Orange was obtained.

After TCDD adsorption, the carbon column was then washed with 300 cc of methylene chloride to remove interstitial liquid and sorbate from the bed but without removing adsorbed TCDD. The carbon was treated in place with condensing vapors from boiling methylene chloride to remove additional sorbate other than TCDD.

The carbon bed was then washed with 2,000 gms of toluene at ambient temperature to remove still more sorbate other than TCDD. To this point no detectable TCDD was found in the liquid regenerants. The carbon was divided into two equal portions. One portion was transferred to the extraction section of a Soxhlet extractor and 200 ml toluene was placed in the boiler portion and boiled to provide extractant. The carbon was so extracted for three hours with refluxing toluene.

After extraction, the toluene in the boiler flask was cooled and analyzed for TCDD. The concentration was 34 ppm of TCDD.

EXAMPLE 6

The TCDD containing toluene solution from Example 5 was placed in a three-necked, 1,000 ml, round-bottomed flask equipped with a thermometer, a reflux condenser with a water trap sidearm, magnetic stirrer, and a heating mantle. Thereafter, 100 gms of TCDD-free dichlorodimethoxybenzene, containing 34.25% organic chlorine, 10 ml of toluene, 80 gms of anhydrous NaOH, and 185 gms of ethylene glycol were introduced. The mixture was heated to 185° C. while withdrawing water and toluene from the water trap. The temperature was maintained at 185° C. for a total of six hours.

Analysis of the resulting mass showed a total conversion of organic to inorganic chloride, with no TCDD detectable.

It is anticipated that disposal of the reaction mass from the preceding Examples 1 to 4, and 6 could be accomplished by drumming for chemical landfill, deep well injection, biological oxidation, or incineration. The reaction mass is very fluid at 100° C. or above. Below 100° C., thinning with water would be necessary for reasonable handling.

It is expected that this process could be utilized for destruction of such materials as PCBs, PBB, DDT, many other halogenated aromatic and cyclic compounds, and halogenated aliphatics.

EXAMPLE 7

TCDD Destruction by Combination Chemical and Extractive Treatment 440 grams of a residue comprising mainly dichloromethoxybenzene and containing 35.73% combined organic chlorine and 240 ppm of tetrachlorodibenzo-p-dioxin (TCDD) were charged to a reactor along with 825.6 grams of ethylene glycol and 886.9 grams of 50% sodium hydroxide solution. 25.2 grams of toluene were added to this mixture. The mixture was heated in the range of 165°–185.5° C. for 8 hours and 45 minutes. During this period, toluene and water of reaction were distilled off. The reaction mass so treated was then analyzed for TCDD by methylene chloride extraction and found to have a dioxin content of 90 ppb, based on the original 440 grams of residue.

The same residue was then heated for another 7 hours and 15 minutes in the same temperature range, and at the end of this time it was analyzed again. The TCDD content of the mass was 25 ppb. based on the original 440 grams of residue.

This residue was then diluted with water to produce a solution containing 35.96 grams of residue per 100 milliliters of solution. 100 ml of this solution was extracted with 100 milliliters of hexane by shaking in a separatory funnel for a minute. The layers were allowed to settle and the hexane layer withdrawn and analyzed for TCDD. It was found to contain 27.50 parts per billion of TCDD based upon the original 35.96 grams of residue. The extracted residue was then analyzed for TCDD and found to contain 0.3 ppb of TCDD. From these analyses, it is computed that the removal of TCDD from the residue by the hexane extraction step was 98.8% Thus, a residue originally containing 240 ppm was chemically treated to produce a residue containing 25 ppb, and 98.8% of that TCDD was further removed by a hexane extraction. Thus, the percent of the TCDD originally present in the residue that was destroyed is computed to be 99.99988%.

The hexane extract was returned to the next batch of 440 grams of residue being treated by the process. The hexane as well as the water and toluene were distilled off during the next reaction. The addition of the hexane extract to the 440 grams of residue containing 240 ppm of TCDD increased the TCDD content about 0.05%.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method for the reduction of the content of chlorinated aromatic dioxins in reaction products to virtually zero consisting essentially of reacting a high boiling still bottom residue containing chlorinated aromatic dioxins resulting from production and distillation of 2,4,5-trichlorophenol with an amount, in excess of stoichiometrical based on the total organic halogen content, of alkaline reactants selected from the group consisting of:
   (1) alkali metal alcoholates of alcohols selected from the group consisting of alkanols having from 1 to 5 carbon atoms, polyalkoxyalkane glycols having from 4 to 20 carbon atoms, alkanepolyols having from 2 to 5 carbon atoms and 2 to 3 hydroxyls, and monoalkyl ethers of said alkanepolyols with alkanols having from 1 to 4 carbon atoms and
   (2) mixtures of said alcohols with alkaline reactants selected from the group consisting of alkali metal hydroxides and carbonates,
at a reaction temperature of from 140° C. to 220° C. for a time sufficient to convert the organic chlorine of the halogenated aromatic compounds in the still bottoms into inorganic chloride, and recovering the still bottoms virtually free of chlorinated aromatic dioxins.

2. The method of claim 1 wherein said alkali metal alcoholates are employed.

3. The method of claim 2 wherein from 1 to 2 equivalents of said alkali metal alcoholate is employed per equivalent of organic halogen, together with from 0.5 to 1 equivalent of said alcohol per equivalent of organic halogen.

4. The method of claim 1 wherein said mixture of said alcohols with said alkaline reactants is employed.

5. The method of claim 4 wherein from 1 to 2 equivalents of said mixture of said alcohols with said alkaline reactants is employed per equivalent of organic halogen.

6. The method of claim 1 wherein the reaction is conducted at atmospheric pressure where said alcohols are said polyalkoxyalkane glycols and said alkanepolyols.

7. The method of claim 1 wherein said high boiling still bottoms containing chlorinated aromatic dioxins contains 2,3,7,8-tetrachlorodibenzo-p-dioxin.

8. The method of claim 1 wherein said still bottoms virtually free of chlorinated aromatic dioxins is substantially dissolved in water, extracted with an organic solvent for chlorinated aromatic dioxins immiscible in water and said organic solvent extract is recycled to said reacting step.

9. A method for the reduction of the content of chlorinated dibenzo-p-dioxins in reaction products to virtually zero consisting of
   (1) reacting a high boiling still bottom residue containing chlorinated dibenzo-p-dioxin resulting from the production and distillation of 2,4,5-trichlorophenol with an amount, in excess of stoichiometrical based on the total organic halogen content, of alkaline reactants selected from the group consisting of:
      (a) alkali metal alcoholates of alcohols selected from the group consisting of alkanols having from 1 to 5 carbon atoms, polyalkoxyalkane glycols having from 4 to 20 carbon atoms, alkanepolyols having from 2 to 5 carbon atoms and 2 to 3 hydroxyls, and monoalkyl ethers of said alkanepolyols with alkanols having from 1 to 4 carbon atoms and
      (b) mixtures of said alcohols with alkaline reactants selected from the group consisting of alkali metal hydroxides and carbonates,
   at a reaction temperature of from 140° C. to 220° C. for a time sufficient to convert substantially all the organic chlorine of the halogenated aromatic compounds in the still bottoms into inorganic chloride, and recovering the still bottoms virtually free of chlorinated dibenzo-p-dioxins
   (2) substantially dissolving the still bottoms virtually free of chlorinated dibenzo-p-dioxins in water,
   (3) extracting the aqueous mass with an organic solvent for chlorinated dibenzo-p-dioxins immiscible in water,
   (4) discharging the extracted aqueous mass vitually free of chlorinated dibenzo-p-dioxins,
   (5) recycling said organic solvent extract to step (1), and
   (6) recovering said organic solvent from said reaction step 1 by distillation and condensation.

10. The method of claim 9 wherein said high boiling still bottom residue containing chlorinated dibenzo-p-dioxins contains over 100 ppm 2,3,7,8-tetrachlorodibenzo-p-dioxin and said discharged extracted aqueous mass contains less than 1 part per billion of 2,3,7,8-tetrachlorodibenzo-p-dioxin.

11. A method for the reduction of the content of chlorinated dibenzo-p-dioxins adsorbed on a solid adsorbent to virtually zero consisting essentially of contacting said solid adsorbent with an aromatic organic liquid at a temperature of between 80° C. and 220° C. for a time sufficient to desorb and dissolve substantially all of said chlorinated dibenzo-p-dioxins, reacting said aromatic organic liquid containing chlorinated dibenzo-p-dioxins with an amount, in excess of stoichiometrical based on the total organic halogen content, of alkaline reactants selected from the group consisting of
   (1) alkali metal alcoholates of alcohols selected from the group consisting of alkanols having from 1 to 5 carbon atoms, polyalkoxyalkane glycols having from 4 to 20 carbon atoms, alkanepolyols having from 2 to 5 carbon atoms and 2 to 3 hydroxyls, and monoalkyl ethers of said alkane polyols with alkanols having from 1 to 4 carbon atoms, and
   (2) mixtures of said alcohols with alkaline reactants selected from the group consisting of alkali metal hydroxides and carbonates,
at a reaction temperature of from 140° C. to 220° C. for a time sufficient to convert the organic halogen into inorganic halide, and recovering a aromatic organic liquid virtually free of chlorinated dibenzo-p-dioxins.

12. The method of claim 11 wherein said solid adsorbent is activated carbon.

13. The method of claim 11 wherein said aromatic organic liquid is toluene.

14. The method of claim 11 wherein said chlorinated dibenzo-p-dioxins include 2,3,7,8-tetrachlorodibenzo-p-dioxin.

* * * * *